US011753394B2

(12) United States Patent
Caille et al.

(10) Patent No.: US 11,753,394 B2
(45) Date of Patent: Sep. 12, 2023

(54) SYNTHESIS OF OMECAMTIV MECARBIL

(71) Applicant: AMGEN INC., Thousand Oaks, CA (US)

(72) Inventors: Sebastien Caille, Thousand Oaks, CA (US); Kyle Quasdorf, Thousand Oaks, CA (US); Philipp C. Roosen, Thousand Oaks, CA (US); Xianqing Shi, Newbury Park, CA (US); Andrew Cosbie, Ventura, CA (US); Fang Wang, Simi Valley, CA (US); Zufan Wu, Walnut, CA (US); Archana Neergunda, Simi Valley, CA (US); Bin Peter Quan, Thousand Oaks, CA (US); Lianxiu Guan, Camarillo, CA (US)

(73) Assignee: AMGEN INC., Thousand Oaks, CA (US)

( * ) Notice: Subject to any disclaimer, the term of this patent is extended or adjusted under 35 U.S.C. 154(b) by 162 days.

(21) Appl. No.: 17/324,867

(22) Filed: May 19, 2021

(65) Prior Publication Data
US 2021/0371397 A1 Dec. 2, 2021

Related U.S. Application Data

(62) Division of application No. 16/607,940, filed as application No. PCT/US2018/040176 on Jun. 29, 2018, now Pat. No. 11,040,956.

(60) Provisional application No. 62/664,363, filed on Apr. 30, 2018, provisional application No. 62/527,174, filed on Jun. 30, 2017.

(51) Int. Cl.
*C07D 401/12* (2006.01)
*C07D 241/04* (2006.01)

(52) U.S. Cl.
CPC ......... *C07D 401/12* (2013.01); *C07D 241/04* (2013.01)

(58) Field of Classification Search
CPC .................................................. C07D 401/12
See application file for complete search history.

(56) References Cited

U.S. PATENT DOCUMENTS

| | | | |
|---|---|---|---|
| 6,492,529 B1 | 12/2002 | Kapadia et al. | |
| 7,507,735 B2 | 3/2009 | Morgan et al. | |
| 8,101,617 B2 | 1/2012 | Morgan et al. | |
| 8,110,595 B2 | 2/2012 | Morgan et al. | |
| 8,445,495 B2 | 5/2013 | Morgan et al. | |
| 8,513,257 B2 | 8/2013 | Morgan et al. | |
| 8,871,768 B2 | 10/2014 | Morgan et al. | |
| 8,871,769 B2 | 10/2014 | Morgan et al. | |
| 9,150,564 B2 | 10/2015 | Morgan et al. | |
| 9,643,925 B2 | 5/2017 | Morgan et al. | |
| 9,895,308 B2 | 2/2018 | Caldwell | |
| 9,951,015 B2 | 4/2018 | Bi et al. | |
| 9,988,354 B2 | 6/2018 | Cui et al. | |
| 10,035,770 B2 | 7/2018 | Morgan et al. | |
| 10,385,023 B2 | 8/2019 | Morgan et al. | |
| 10,421,726 B2 | 9/2019 | Bi et al. | |
| 10,543,215 B2 | 1/2020 | Scott et al. | |
| 10,975,034 B2 | 4/2021 | Morgan et al. | |
| 11,040,956 B2 | 6/2021 | Caille et al. | |
| 11,384,053 B2 | 7/2022 | Bi et al. | |
| 11,465,969 B2 | 10/2022 | Morrison et al. | |
| 11,472,773 B2 | 10/2022 | Cui et al. | |
| 11,576,910 B2 | 2/2023 | Honarpour et al. | |
| 2006/0014761 A1 | 1/2006 | Morgan et al. | |
| 2007/0161617 A1 | 7/2007 | Morgan et al. | |
| 2009/0036447 A1 | 2/2009 | Morgan et al. | |
| 2009/0099198 A1 | 4/2009 | Morgan et al. | |
| 2009/0192168 A1 | 7/2009 | Muci et al. | |
| 2010/0029680 A1 | 2/2010 | Morgan et al. | |
| 2012/0172372 A1 | 7/2012 | Morgan et al. | |
| 2013/0324549 A1 | 12/2013 | Morgan et al. | |
| 2014/0038983 A1 | 2/2014 | Morgan et al. | |
| 2014/0309235 A1 | 10/2014 | Bi et al. | |
| 2015/0005296 A1 | 1/2015 | Morgan et al. | |
| 2016/0015628 A1 | 1/2016 | Caldwell | |
| 2016/0016906 A1 | 1/2016 | Cui et al. | |
| 2016/0115133 A1 | 4/2016 | Morgan et al. | |
| 2017/0267638 A1 | 9/2017 | Morgan et al. | |
| 2018/0140611 A1 | 5/2018 | Scott et al. | |
| 2018/0273479 A1 | 9/2018 | Bi et al. | |
| 2018/0305316 A1 | 10/2018 | Morgan et al. | |
| 2018/0312469 A1 | 11/2018 | Cui et al. | |
| 2019/0352267 A1 | 11/2019 | Morgan et al. | |
| 2020/0079736 A1 | 3/2020 | Cui et al. | |
| 2020/0108076 A1 | 4/2020 | Scott et al. | |
| 2020/0155547 A1 | 5/2020 | Honarpour et al. | |
| 2020/0277261 A1 | 9/2020 | Bi et al. | |
| 2020/0308143 A1 | 10/2020 | Caille et al. | |
| 2020/0331859 A1 | 10/2020 | Cui et al. | |
| 2020/0399221 A1 | 12/2020 | Cui et al. | |

(Continued)

FOREIGN PATENT DOCUMENTS

CN 105120844 A 12/2015
IN 202111035890 A 3/2023

(Continued)

OTHER PUBLICATIONS

International Preliminary Report on Patentability, dated Dec. 31, 2019 for Patent Application No. PCT/US2018/040176, filed Jun. 29, 2018, 11 pages.
International Search Report and Written Opinion of the International Searching Authority dated Nov. 7, 2018, for Patent Application No. PCT/US2018/040176, filed Jun. 29, 2018, 20 pages.
Swanson et al. (Mar. 2005). "Identification And Biological Evaluation Of 4-(3-Trifluoromethylpyridin-2-YI) Piperazine-1-Carboxylic Acid (5-Trifluoromethylpyridin-2-YI) Amide, A High Affinity TRPV1 (VR1) Vanilloid Receptor Antagonist," Journal Of Medicinal Chemistry 48(6):1857-1872.

(Continued)

*Primary Examiner* — Bruck Kifle
(74) *Attorney, Agent, or Firm* — Morrison & Foerster LLP

(57) ABSTRACT

Provided herein is a synthesis for omecamtiv mecarbil dihydrochloride hydrate and various intermediates.

7 Claims, 3 Drawing Sheets

(56) References Cited

U.S. PATENT DOCUMENTS

| | | |
|---|---|---|
| 2021/0198203 A1 | 7/2021 | Morgan et al. |
| 2021/0221772 A1 | 7/2021 | Man et al. |
| 2021/0292271 A1 | 9/2021 | Brasola et al. |
| 2022/0042055 A1 | 2/2022 | Bisagni et al. |
| 2022/0153700 A1 | 5/2022 | Cui et al. |
| 2022/0184068 A1 | 6/2022 | Honarpour et al. |
| 2022/0185779 A1 | 6/2022 | Morgan et al. |
| 2022/0298099 A1 | 9/2022 | Caille et al. |
| 2022/0298114 A1 | 9/2022 | Bi et al. |
| 2023/0044617 A1 | 2/2023 | Cui et al. |
| 2023/0090391 A1 | 3/2023 | Bi et al. |

FOREIGN PATENT DOCUMENTS

| | | |
|---|---|---|
| JP | 2009519939 A | 5/2009 |
| JP | 2010506896 A | 3/2010 |
| JP | 2016519071 A | 6/2016 |
| TW | 201625568 A | 7/2016 |
| WO | 2007070626 A2 | 6/2007 |
| WO | 2007078839 A2 | 7/2007 |
| WO | 2008047229 A2 | 4/2008 |
| WO | 2010141817 A1 | 12/2010 |
| WO | 2014152198 A1 | 9/2014 |
| WO | 2014152270 A1 | 9/2014 |
| WO | 2015152236 A1 | 10/2015 |
| WO | 2016082930 A1 | 6/2016 |
| WO | 2019006231 A1 | 1/2019 |
| WO | 2021070124 A1 | 4/2021 |

OTHER PUBLICATIONS

Thavonekham, B. (Oct. 1997). "A Practical Synthesis Of Ureas From Phenyl Carbamates," Synthesis 1997 (10):1189-1194.

U.S. Appl. No. 15/898,303, filed Feb. 16, 2018, by William Brett Caldwell et al. (The U.S. Patent Application is not submitted herewith pursuant to the waiver of 37 C.F.R. § 1.98(a)(2)(iii) issued by the Office on Sep. 21, 2004.).

U.S. Appl. No. 17/176,003, filed Feb. 15, 2021, by Sheng Cui et al. (The U.S. Patent Application is not submitted herewith pursuant to the waiver of 37 C.F.R. § 1.98(a)(2)(iii) issued by the Office on Sep. 21, 2004.).

U.S. Appl. No. 17/258,385, filed Jan. 6, 2021, by Elena Brasola et al. (The U.S. Patent Application is not submitted herewith pursuant to the waiver of 37 C.F.R. § 1.98(a)(2)(iii) issued by the Office on Sep. 21, 2004.).

U.S. Appl. No. 17/263,224, filed Jan. 26, 2021, by Henry Morrison et al. (The U.S. Patent Application is not submitted herewith pursuant to the waiver of 37 C.F.R. § 1.98(a)(2)(iii) issued by the Office on Sep. 21, 2004.).

U.S. Appl. No. 17/309,727, filed Jun. 16, 2021, by Serena Bisagni et al. (The U.S. Patent Application is not submitted herewith pursuant to the waiver of 37 C.F.R. § 1.98(a)(2)(iii) issued by the Office on Sep. 21, 2004.).

U.S. Appl. No. 17/929,645, filed Sep. 2, 2022, by Henry Morrison et al. (The U.S. Patent Application is not submitted herewith pursuant to the waiver of 37 C.F.R. § 1.98(a)(2)(iii) issued by the Office on Sep. 21, 2004.).

U.S. Appl. No. 18/155,483, filed Jan. 17, 2023, by Narimon, Honarpour et al. (The U.S. Patent Application is not submitted herewith pursuant to the waiver of 37 C.F.R. § 1.98(a)(2)(iii) issued by the Office on Sep. 21, 2004.).

SYNTHESIS OF OMECAMTIV MECARBIL

CROSS REFERENCE TO RELATED APPLICATIONS

This application is a divisional of U.S. patent application Ser. No. 16/607,940, which adopts an international filing date of Jun. 29, 2018, now U.S. Pat. No. 11,040,956, which is the national stage application under 35 U.S.C. § 371 of International Application No. PCT/US2018/040176, filed internationally on Jun. 29, 2018, which claims benefit of U.S. Provisional Patent Application Nos. 62/664,363, filed Apr. 30, 2018, and 62/527,174, filed Jun. 30, 2017, the disclosures of which are herein incorporated by reference in their entirety.

FIELD

Provided are methods of preparing omecamtiv mecarbil and new intermediates of omecamtiv mecarbil, and intermediate synthetic methods.

BACKGROUND

The cardiac sarcomere is the basic unit of muscle contraction in the heart. The cardiac sarcomere is a highly ordered cytoskeletal structure composed of cardiac muscle myosin, actin and a set of regulatory proteins. The discovery and development of small molecule cardiac muscle myosin activators would lead to promising treatments for acute and chronic heart failure and dilated cardiomyopathy (DCM) and conditions associated with left and/or right ventricular systolic dysfunction or systolic reserve. Cardiac muscle myosin is the cytoskeletal motor protein in the cardiac muscle cell. It is directly responsible for converting chemical energy into the mechanical force, resulting in cardiac muscle contraction.

Current positive inotropic agents, such as beta-adrenergic receptor agonists or inhibitors of phosphodiesterase activity, increase the concentration of intracellular calcium, thereby increasing cardiac sarcomere contractility. However, the increase in calcium levels increase the velocity of cardiac muscle contraction and shortens systolic ejection time, which has been linked to potentially life-threatening side effects. In contrast, cardiac muscle myosin activators work by a mechanism that directly stimulates the activity of the cardiac muscle myosin motor protein, without increasing the intracellular calcium concentration. They accelerate the rate-limiting step of the myosin enzymatic cycle and shift it in favor of the force-producing state. Rather than increasing the velocity of cardiac contraction, this mechanism instead lengthens the systolic ejection time, which results in increased cardiac muscle contractility and cardiac output in a potentially more oxygen-efficient manner.

U.S. Pat. No. 7,507,735, herein incorporated by reference, discloses a genus of compounds, including omecamtiv mecarbil (AMG 423, CK-1827452), having the structure:

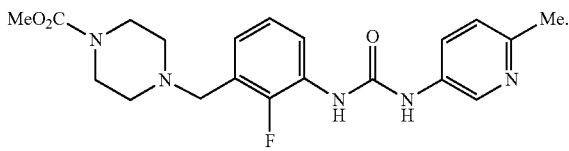 [SMILES: COC(=O)N1CCN(Cc2cccc(NC(=O)Nc3ccc(C)nc3)c2F)CC1]

Omecamtiv mecarbil is a first in class direct activator of cardiac myosin, the motor protein that causes cardiac contraction. It is being evaluated as a potential treatment of heart failure in both intravenous and oral formulations with the goal of establishing a new continuum of care for patients in both the in-hospital and outpatient settings.

There is an ongoing need for a commercial process of manufacture of omecamtiv mecarbil that addresses the issues specific to API production, including good manufacturing procedure (GMP) requirements and regulatory body approval (e.g., the US FDA and the EMA).

SUMMARY

Provided herein is piperazine methyl carboxylate (PMEC) phosphate salt, e.g., a PMEC phosphate hydrate salt. PMEC is alternatively referred to as methyl piperazine-1-carboxylate.

Further provided herein are processes of synthesizing PMEC phosphate salt comprising a) admixing piperazine and methyl chloroformate to form PMEC; (b) admixing the PMEC and 0.5 molar equivalents of phosphoric acid to form PMEC phosphate; and (c) optionally filtering the PMEC phosphate from the admixture of step (b). In some cases, step (a) is performed in an aqueous solution which generates PMEC phosphate hydrate with a PMEC to water ratio of about 2:1. In various cases, step (a) is performed at a temperature of 20 to 55° C. for 1 to 12 hours. In some cases, the PMEC formed in step (a) is isolated as a solution in methylene chloride, dichloroethane, 2-methyltetrahydrofuran, or mixture thereof. More specifically, the isolation can be performed by (i) washing the resulting PMEC from step (a) with an organic solvent; (ii) modifying the pH to 8 to 14 by adding a base to form a basic aqueous solution; and (iii) extracting the PMEC from the basic aqueous solution of step (ii) with methylene chloride, dichloroethane, 2-methyl tetrahydrofuran, or mixture thereof.

Also provided herein are processes of synthesizing methyl 4-(2-fluoro-3-nitrobenzyl)piperazine-1-carboxylate (PIPN) comprising (a) admixing 2-fluoro-3-nitrotoluene, sodium bromate, and sodium bisulfite in isopropylacetate and water to form 1-(bromomethyl)-2-fluoro-3-nitrobenzene (FNB); (b) optionally washing the FNB with aqueous sodium thiosulfate, with aqueous sodium chloride, or both; and (c) admixing FNB, a trialkylamine base, and piperazine methyl carboxylate ("PMEC") phosphate, e.g., PMEC phosphate hydrate, to form PIPN. In some cases, the FNB is washed with aqueous sodium thiosulfate, and aqueous sodium chloride. Alternatively, PIPN can be prepared by (a) admixing 2-fluoro-3-nitrotoluene, benzoyl peroxide, N-bromosuccinimide and acetic acid at a temperature of 70 to 95° C. to form 1-(bromomethyl)-2-fluoro-3-nitrobenzene (FNB); (b) optionally extracting FNB with toluene, washing FNB with an aqueous basic solution, or both; (c) admixing FNB, a trialkylamine base, and piperazine methyl carboxylate ("PMEC") phosphate, e.g., PMEC phosphate hydrate, to form PIPN. In some cases, FNB is extracted with toluene and washed with aqueous sodium hydroxide. In either process for preparing PIPN, the PIPN can be formed as a hydrochloride salt. In either process for preparing PIPN, the PMEC phosphate, e.g., PMEC phosphate hydrate, can be prepared as disclosed herein. In either process for preparing PIPN, the trialkylamine base comprises diisopropylethylamine or triethylamine. In either process for preparing PIPN, prior to admixing the FNB, the trialkylamine base, and the PMEC, the process can further comprise adding diethylphosphite and a trialkylamine, and admixing the resulting mixture at a temperature of 30 to 65° C.

Further provided herein are processes for synthesizing phenyl (6-methylpyridin-3-yl) carbamate (PCAR) comprising admixing 5-amino-2-methylpyridine (APYR) and phenyl chloroformate in acetonitrile to form PCAR, wherein the admixing is performed in the absence of N-methyl pyrrolidinone (NMP). In some cases, the admixing is performed at a temperature of 15 to 30° C. for 1 to 15 hours. In various cases, the PCAR is formed as a hydrochloride salt. In some cases, the process can further comprise preparing APYR by a process comprising: (i) hydrogenating 2-methyl-5-nitropyridine (NPYR) in the presence of a palladium catalyst to form crude APYR; and (ii) crystallizing APYR from the crude APYR in isopropyl acetate and heptane. In various cases, the process can further comprise, prior to step (i), washing NPYR in isopropyl acetate with aqueous sodium hydroxide, followed by admixing the washed NPYR in isopropyl acetate with charcoal. In some cases, the process can further comprise, prior to admixing the APYR and phenyl chloroformate, purifying APYR by a process comprising: (i) washing an isopropyl acetate solution of crude APYR, wherein the crude APYR comprises up to 10 wt % APYR hydrochloride, with aqueous sodium hydroxide, and admixing the washed APYR with charcoal to form, after filtration, an APYR solution; and (ii) crystallizing APYR from the APYR solution of step (i) from isopropyl acetate and heptane. In various cases, the process can further comprise crystallizing PCAR.

Also provided herein are processes for synthesizing methyl 4-(3-amino-2-fluorobenzyl)piperazine-1-carboxylate (PIPA) comprising (a) admixing methyl 4-(2-fluoro-3-nitrobenzyl)piperazine-1-carboxylate (PIPN), an aqueous solution of an inorganic base, and toluene to form a PIPN freebase solution; (b) hydrogenating the PIPN freebase solution in the presence of a palladium catalyst in a toluene and alcohol solvent mixture to form crude PIPA, wherein the alcohol comprises ethanol or isopropanol; and (c) crystallizing the PIPA from the crude PIPA in heptane and toluene. In various cases, the inorganic base comprises sodium hydroxide.

Further provided herein are processes for preparing omecamtiv mecarbil dihydrochloride hydrate comprising (a) admixing methyl 4-(3-amino-2-fluorobenzyl)piperazine-1-carboxylate (PIPA), phenyl (6-methylpyridin-3-yl) carbamate (PCAR), and a trialkylamine in acetonitrile and tetrahydrofuran to form a solution of crude omecamtiv mecarbil; (b) isolating omecamtiv mecarbil free base from the solution of crude omecamtiv mecarbil; and (c) admixing the isolated omecamtiv mecarbil free base with 2 to 3 molar equivalents of hydrochloric acid in isopropanol and water to form omecamtiv mecarbil dihydrochloride hydrate. In various cases, the trialkylamine comprises diisopropylethylamine or triethylamine. In some cases, the isolation of step (b) comprises crystallizing omecamtiv mecarbil free base by adding water to the solution of crude omecamtiv mecarbil from step (a) and filtering the crystallized omecamtiv mecarbil free base. In various cases, the process can further comprise crystallizing the omecamtiv mecarbil dihydrochloride hydrate from isopropanol and water. In some cases, the PCAR is prepared using a process as disclosed herein.

Also provided herein are processes for preparing omecamtiv mecarbil dihydrochloride hydrate comprising (a) admixing methyl 4-(3-amino-2-fluorobenzyl)piperazine-1-carboxylate (PIPA), triphosgene, and a trialkylamine in acetonitrile and tetrahydrofuran to form PIPA isocyanate; (b) admixing the PIPA isocyanate and 5-amino-2-methylpyridine (APYR) to form omecamtiv mecarbil free base; (c) admixing the omecamtiv mecarbil free base with 2 to 3 molar equivalents of hydrochloric acid in isopropanol and water to form omecamtiv mecarbil dihydrochloride hydrate. In some cases, step (a) is performed via continuous manufacturing comprising admixing a first solution comprising PIPA and the trialkylamine in acetonitrile and a second solution comprising triphosgene in tetrahydrofuran using a micromixer chip and a reaction loop to form the PIPA isocyanate. In various cases, step (b) is performed via continuous manufacturing comprising admixing a solution comprising the PIPA isocyanate and a solution comprising the APYR using a Y-mixer and a reaction loop. In some cases, the APYR is prepared via a process as disclosed herein. In some cases, the PIPA is prepared via a process as disclosed herein.

DETAILED DESCRIPTION

Figure 1:
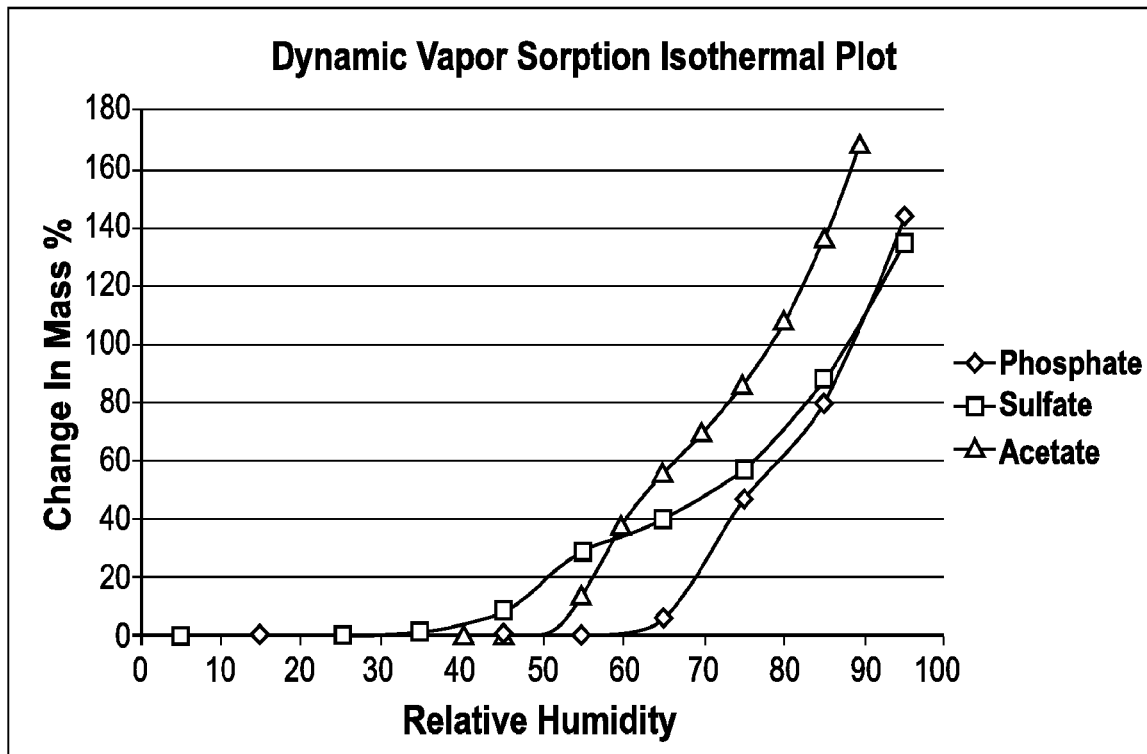
FIG. 1 shows a dynamic vapor sorption (DVS) isothermal plot for three salt forms of methyl piperazine-1-carboxylate (PMEC)—a phosphate hydrate salt form, a hemi-sulfate salt form, and an acetate salt form. The DVS weight increase onset for each salt was measured as noted—35% relative humidity (RH) for the hemi-sulfate; 50% RH for the acetate; and 65% RH for the phosphate hydrate. The phosphate hydrate is termed phosphate or hemi-phosphate and the hemi-sulfate is termed sulfate or hemi-sulfate in the figure.

Omecamtiv mecarbil dihydrochloride hydrate is used in an oral formulation as a treatment of heart failure. Specific conditions include, but are not limited to, acute (or decompensated) congestive heart failure, and chronic congestive heart failure; particularly diseases associated with systolic heart dysfunction.

A prior process to manufacture omecamtiv mecarbil dihydrochloride hydrate is disclosed in WO 2014/152270. The GMP manufacturing sequence disclosed herein differs from that prior synthetic sequence in a number of ways. The GMP sequence is elongated from two to six steps. This longer GMP sequence provides alternative sequences of production, including avoiding solvents during production that are difficult to remove (e.g., N-methylpyrrolidone, NMP), avoiding using an evaporative crystallization, and isolating intermediates to avoid challenging solvent exchanges.

The prior process to manufacture omecamtiv mecarbil dihydrochloride hydrate is depicted in Scheme 1, and is discussed in detail in WO 2014/152270. That process involves the non-GMP preparation of regulatory API starting materials Piperazine Nitro-HCl (PIPN) and Phenyl Carbamate-HCl (PCAR) from commercially available raw materials FN-Toluene (FNT) and 5-Amino-2-methylpyridine (APYR), respectively. Isolated GMP intermediate Piperazine Aniline (PIPA) is prepared from PIPN via hydrogenation and subsequently coupled with PCAR to generate omecamtiv mecarbil. The dihydrochloride hydrate salt of omecamtiv mecarbil is manufactured from the corresponding freebase via a telescoped process (i.e., omecamtiv mecarbil freebase is not isolated) and isolated as a dihydrochloride hydrate by filtration after wet milling. All the API starting materials are noted in boxes.

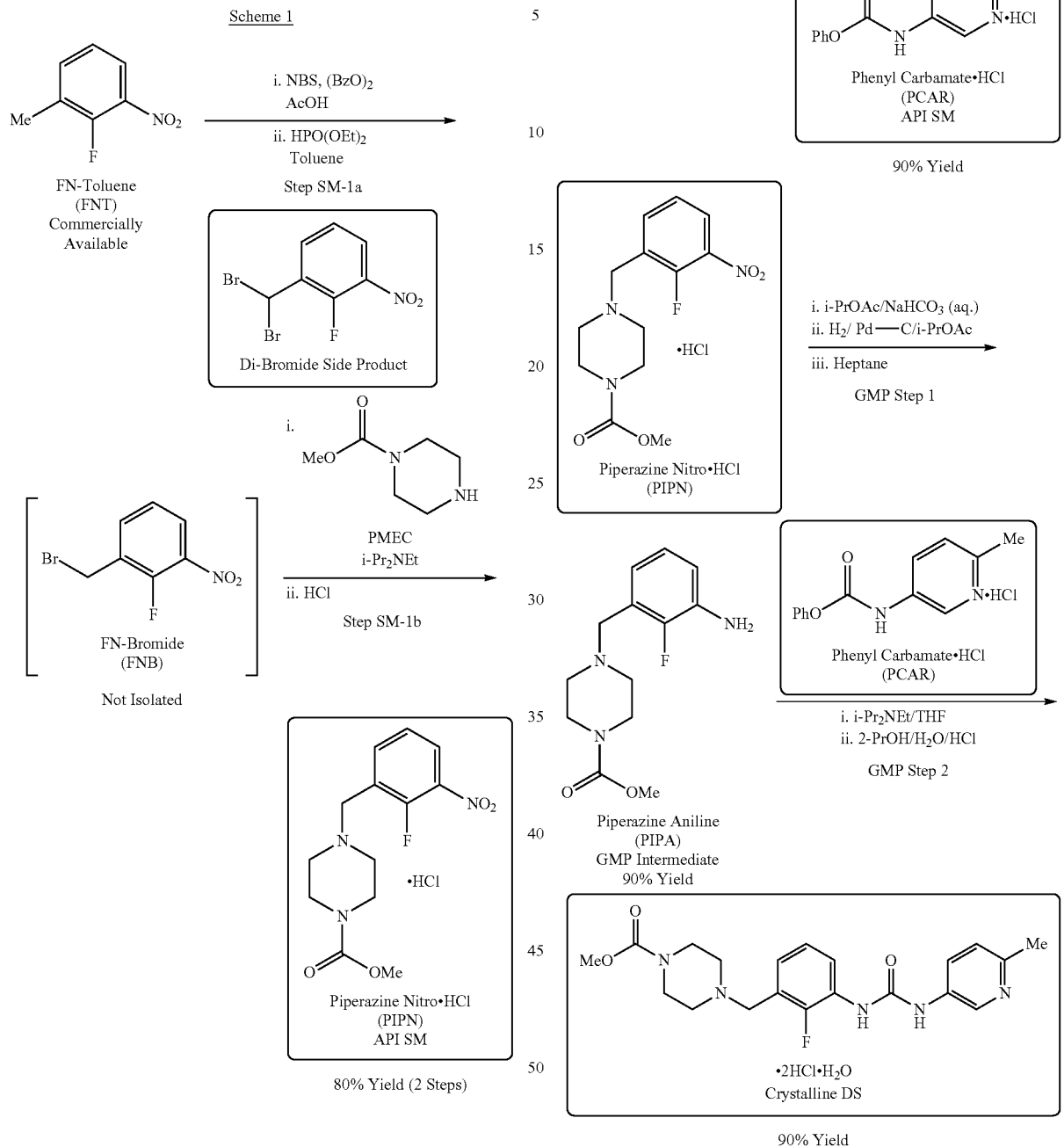

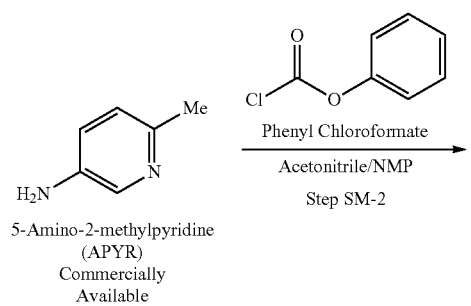

For the synthesis disclosed herein, the API starting materials were moved upstream in the sequence in order to accommodate the requirements for selection and justification of API starting materials to various regulatory bodies, e.g., the EMA and the FDA. As such, the disclosed process herein comprises six steps, compared to the two-step sequence disclosed in WO 2014/152270. This elongated GMP sequence provides several advantages over the shorter sequence. Methyl piperazine-1-carboxylate (PMEC) phosphate is used instead of PMEC free base in the formation of the intermediate piperazine nitro-HCl (PIPN). PMEC free base is an oil that contains various levels of piperazine, which leads to the formation of impurities (e.g., BISN in the product PIPN, see Scheme 3). In contrast, PMEC phosphate is a stable crystalline salt that has low and constant levels of piperazine. Therefore, use of the PMEC hemi-phosphate hemi-hydrate in place of the PMEC free base significantly decreases the formation of impurities. The process disclosed herein also allows for the discontinuation of N-methylpyrrolidinone (NMP) when preparing PCAR, an advantage considering that NMP is difficult to remove and has appeared on REACH protocol lists in the EU (a safety list of chemical materials). In addition, the process disclosed herein alters the solvent in which the hydrogenation of PIPN to generate PIPA is conducted, since the use of isopropyl acetate in the previous process involved an evaporative crystallization operation, which often led to material fouling and inconsistent results. The disclosed process herein replaces a challenging solvent exchange, taking into account the very low solubility of omecamtiv mecarbil freebase in isopropanol (~12 mg/mL) at 20° C. and the formation of an unstirrable slurry during the solvent exchange from tetrahydrofuran (THF) to isopropanol.

The new commercial process disclosed herein to prepare omecamtiv mecarbil dihydrochloride hydrate is shown in Scheme 2. It involves six GMP steps. The designated commercial API starting materials are 2-fluoro-3-nitro-toluene (FNT), 5-Amino-2-methylpyridine (APYR), and PMEC phosphate hydrate.

Scheme 2

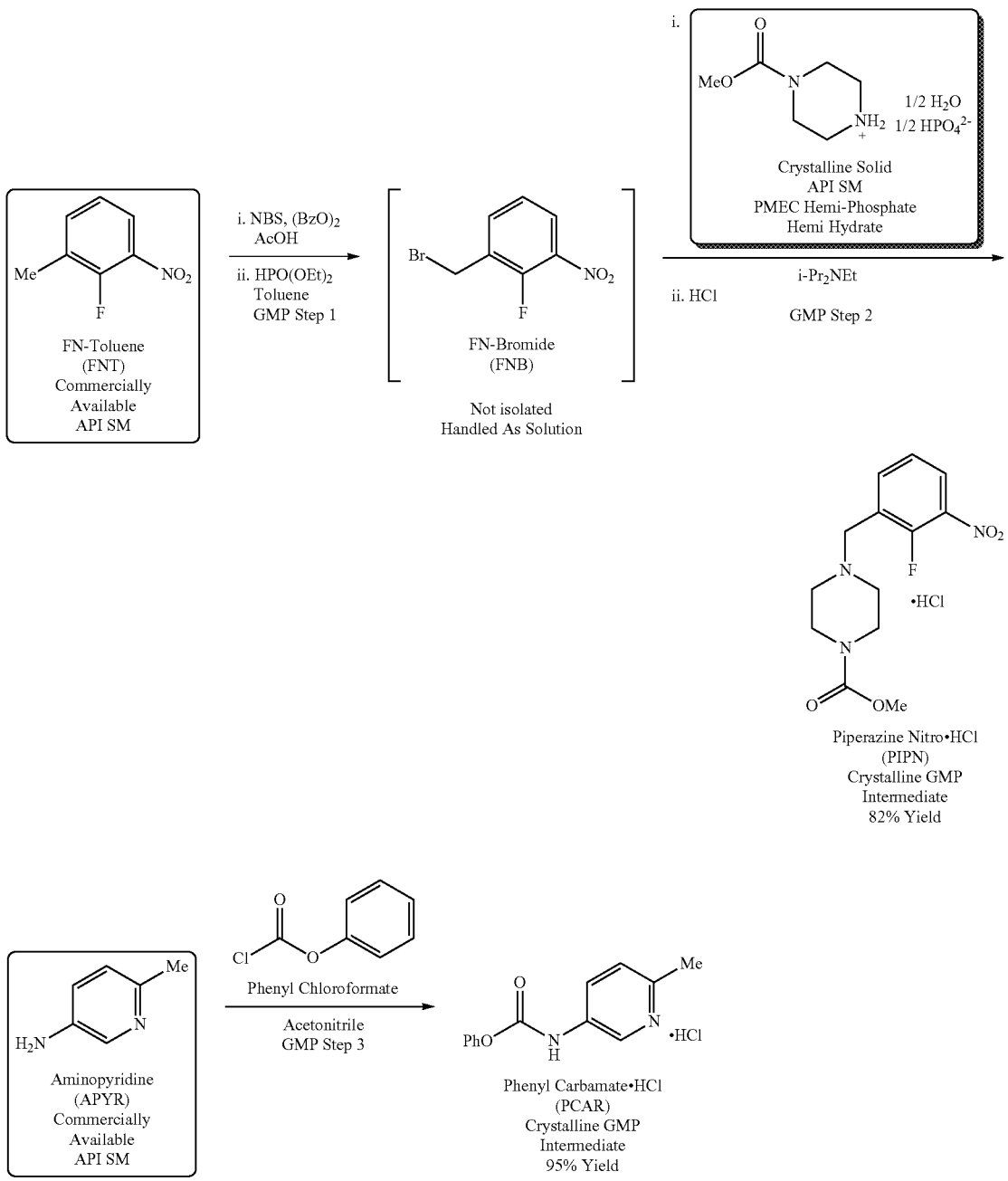

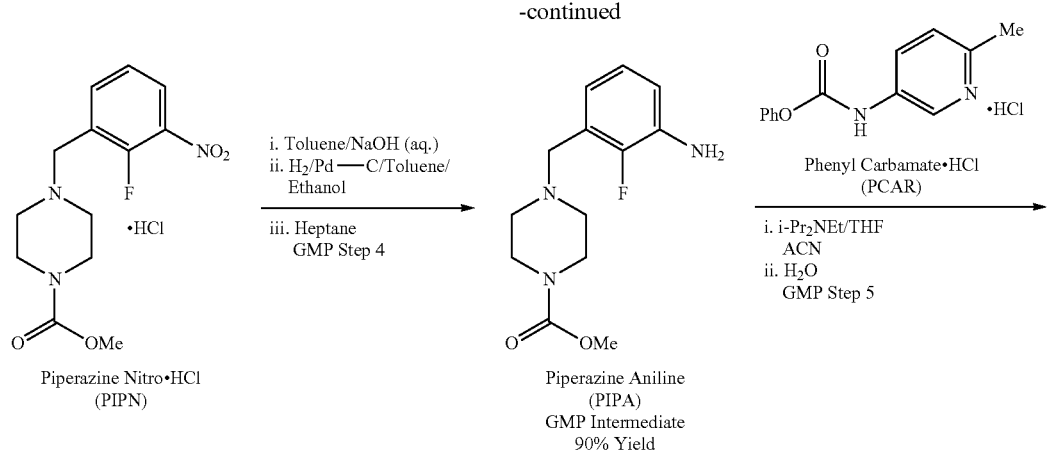

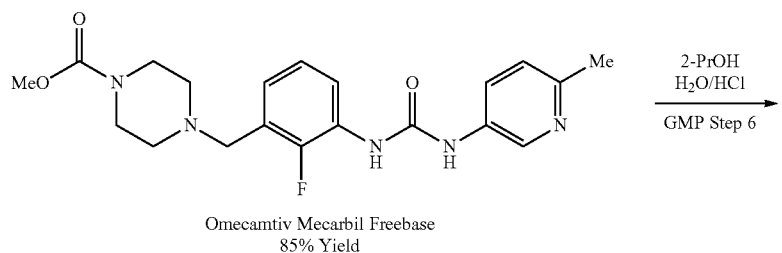

Omecamtiv Mecarbil Freebase
85% Yield

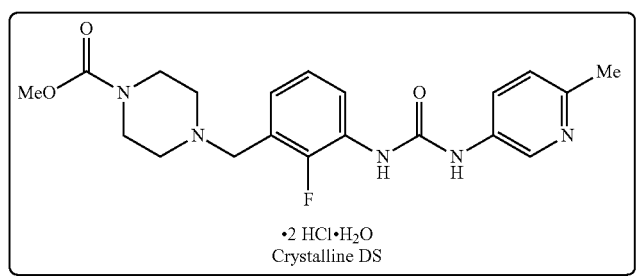

•2 HCl•H$_2$O
Crystalline DS

95% Yield

FN-Toluene is a raw material that is manufactured from toluene using a short synthetic sequence. Fractional distillation of the mixture of isomers generated affords the desired regioisomer 2-fluoro-3-nitro-toluene in acceptable purity, with no greater than 0.5 GC area % of any other isomers. 2-Fluoro-3-nitro-toluene (FNT) manufactured using this process has reproducible quality and it can be designated as a commercial API starting material.

PIPN Manufacture: PMEC phosphate, e.g., PMEC phosphate hydrate, is an API starting material prepared in a single step from piperazine. The prior process to prepare PIPN used PMEC freebase as a raw material, which can be purchased, but is an oil that contains various amounts of piperazine. Upon storage at 25° C., piperazine levels up to 18 LC area % were observed in PMEC freebase. As illustrated in Scheme 3, residual piperazine leads to the formation of impurity BISN in product PIPN.

Scheme 3

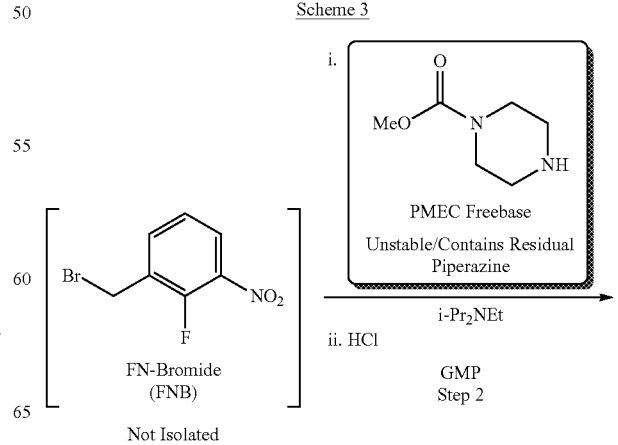

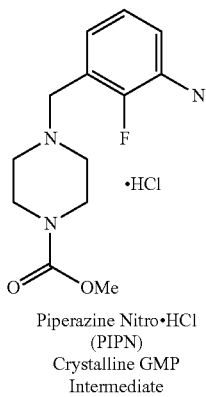

Piperazine Nitro•HCl
(PIPN)
Crystalline GMP
Intermediate

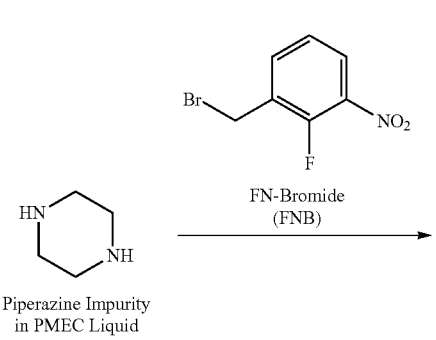

Piperazine Impurity
in PMEC Liquid

FN-Bromide
(FNB)

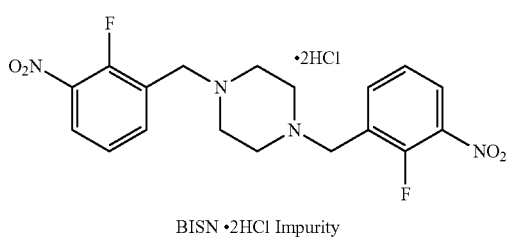

BISN •2HCl Impurity

A stable crystalline salt of PMEC having low and constant levels of piperazine was sought as a commercial API starting material. Multiple salts were thus screened to identify a suitable candidate. PMEC phosphate, e.g., PMEC phosphate hydrate, was found to be less hygroscopic than the corresponding sulfate and acetate salt, as depicted in FIG. 1. It can be stored in air-sealed aluminum bags to avoid contact with moisture.

As a benefit, PMEC phosphate, e.g., PMEC phosphate hydrate, can be added directly to a reaction mixture to prepare PIPN. By contrast, PMEC acetate has to be converted to PMEC freebase prior to addition to the reaction mixture considering the formation of a side-product from FN-Bromide (FNB) and the acetate anion. PMEC phosphate, e.g., PMEC phosphate hydrate, contains low levels of piperazine (<0.4 GC area %) that do not increase upon storage. PMEC phosphate, e.g., PMEC phosphate hydrate, has successfully been utilized for manufacture of PIPN. The batch of PIPN thus manufactured (5 kg) contained less than 0.1 LC area % of residual BISN.

Figure 2:
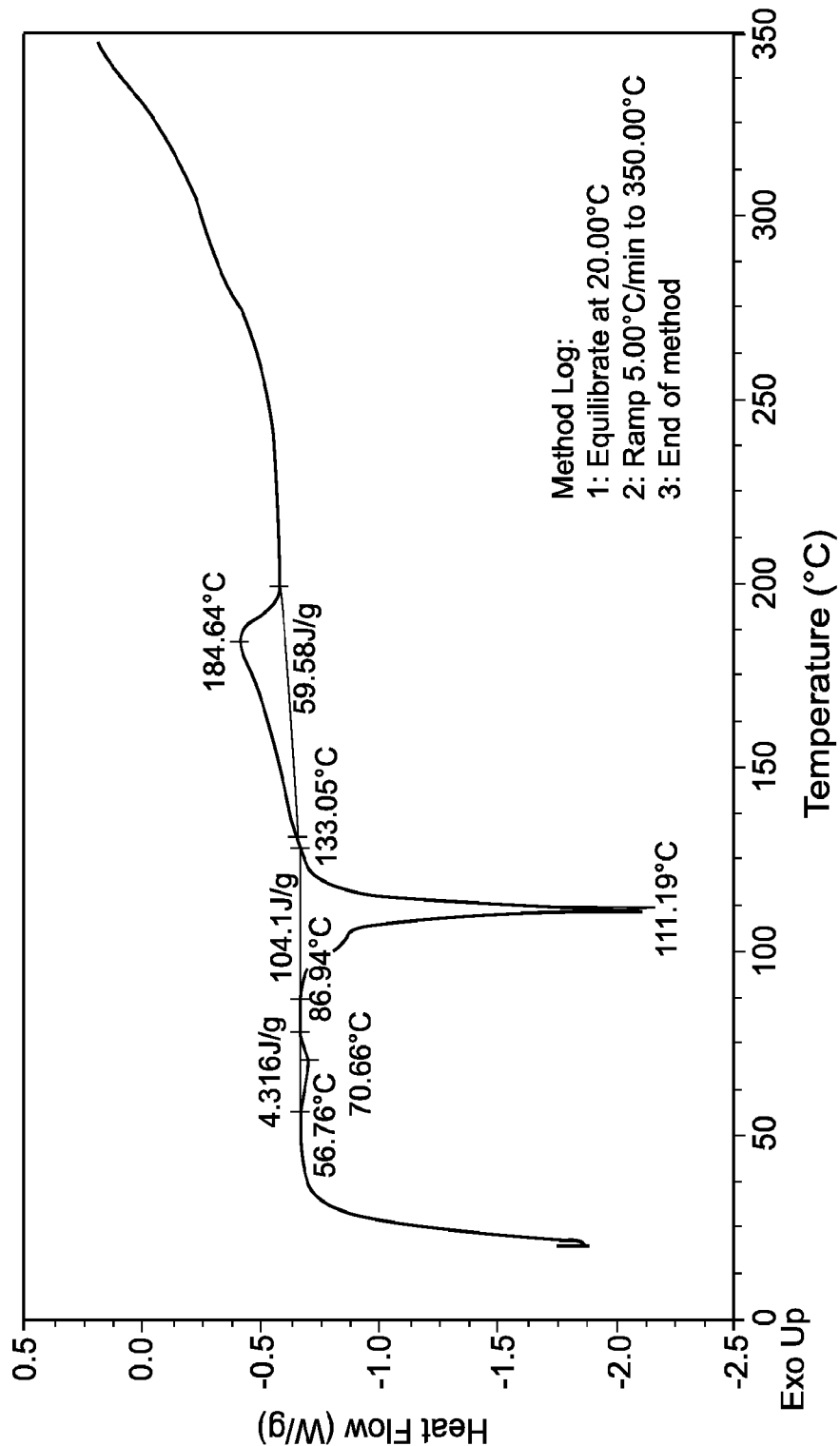
FIG. 2 shows a differential scanning calorimetry spectrum of PMEC phosphate hydrate.
Figure 3:
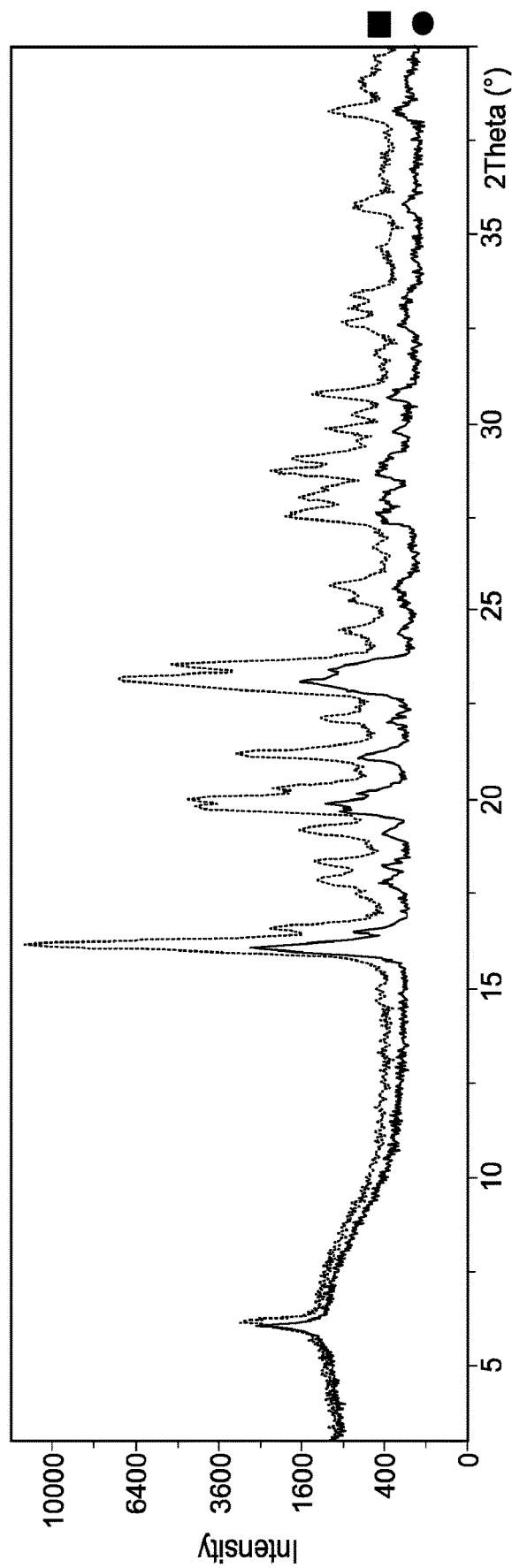
FIG. 3 shows a x-ray powder diffraction pattern for PMEC phosphate hydrate (square) and PMEC slurry (circle).

A process was developed to manufacture PMEC phosphate hydrate involving treatment of piperazine with methyl chloroformate followed by extraction of PMEC as a freebase in the organic layer after neutralization with aqueous sodium hydroxide, as shown in Scheme 4. Subsequent to solvent exchange from dichloromethane to t-butylmethyl ether, the target salt is crystallized by addition of phosphoric acid and filtration. PMEC phosphate hydrate is isolated in 45-50% yield from piperazine and >99 GC area %. Piperazine levels in samples of PMEC phosphate hydrate have been observed to be <0.4 GC area %. DSC spectrum and XRPD pattern for PMEC phosphate hydrate are shown in FIGS. 2 and 3, respectively. PMEC phosphate has a stoichiometry of about 2:1 of PMEC:phosphate and thus is referenced herein interchangeably as PMEC phosphate, or PMEC hemi-phosphate, PMEC phosphate salt. A hydrate of PMEC phosphate can be formed as detailed herein, and such hydrate has a stoichiometry of about 2:1:1 PMEC:phosphate:water, and is referenced interchangeably as PMEC phosphate hydrate, PMEC hemi-phosphate hemi-hydrate, or PMEC phosphate hydrate. It is understood that the ratio of PMEC, phosphate, and water in the PMEC phosphate hydrate may differ slightly from the 2:1:1 stoichiometric ratio noted above, e.g., to a ratio of 6:4:3 or the like. Elemental analysis and/or single crystal X-ray structural analysis can be performed on the material prepared via the processes disclosed herein. The ratio of the PMEC, phosphate, and water in the isolated salt is consistent and determination of the exact ratio of PMEC:phosphate:water does not negatively impact the suitability of the PMEC phosphate hydrate salt herein for the intended use as a starting material in the preparation of omecamtiv mecarbil dihydrochloride hydrate.

Scheme 4

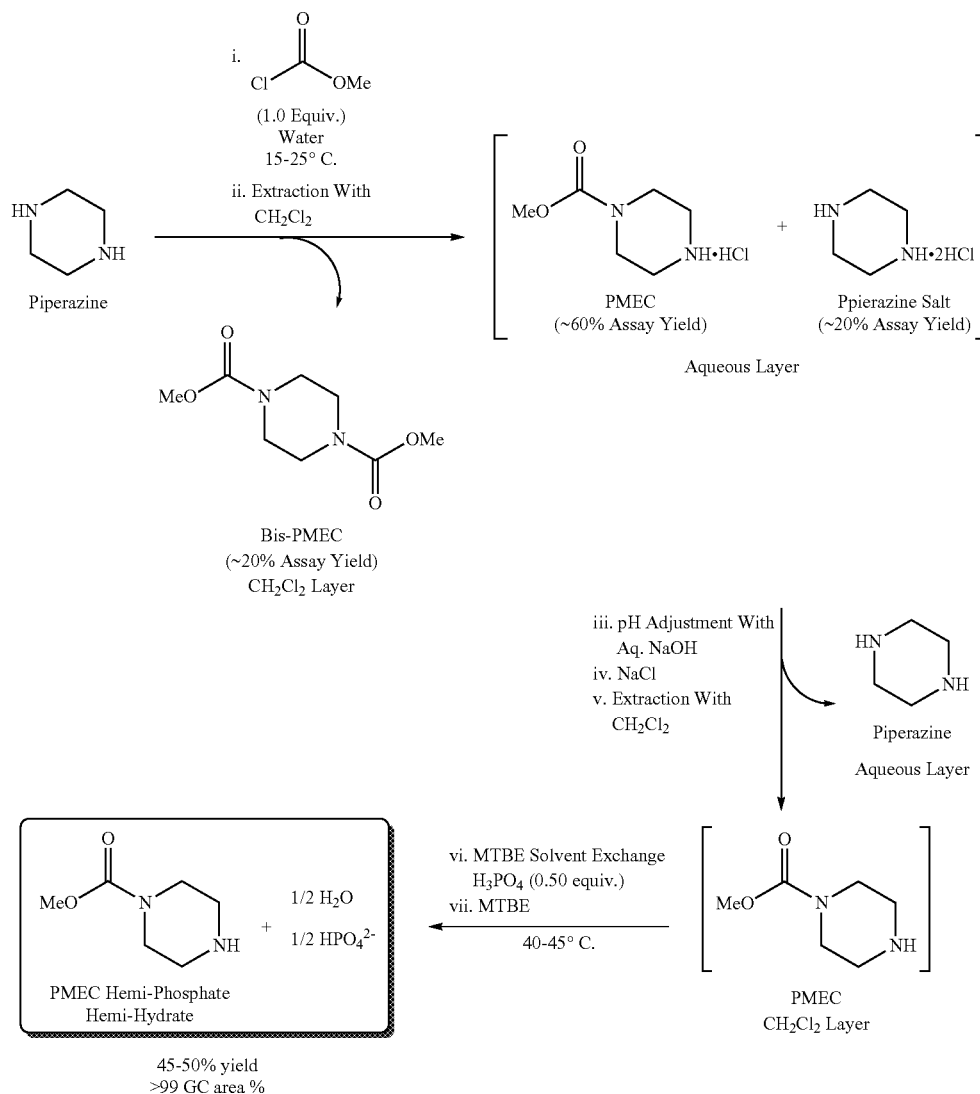

The general synthetic method for preparation of PMEC phosphate, e.g., PMEC phosphate hydrate, comprises admixing piperazine and methyl chloroformate to form PMEC, adding 0.5 molar equivalents of phosphoric acid (e.g., in an aqueous solution) to form the phosphate salt and optionally filtering the salt. The reaction of piperazine and methyl chloroformate can be performed at a temperature of 20 to 55° C. for 1 to 12 hours.

Specific extraction methods and post-reaction work up procedures are shown in Scheme 4 to purify the PMEC phosphate. However, other work up procedures can be employed. The PMEC can be purified from the bis-PMEC formed in the reaction mixture of piperazine and methylchloroformate by extraction with an organic solvent such as methylene chloride, dichloroethane, or 2-methyltetrahydrofuran, or a mixture thereof. In some embodiments, the organic solvent comprises methylene chloride. The undesired bis-PMEC is separated into the organic solvent layer and the desired PMEC remains in the aqueous layer. PMEC can be further purified. For example, PMEC in the aqueous solution can be adjusted to a basic pH (e.g., 8 to 14) by addition of a basic aqueous solution and extracted with an organic solvent, such as methylene chloride, dichloroethane, or 2-methyltetrahydrofuran or a mixture thereof, where the PMEC is in the organic solvent. In some cases, the organic solvent comprises methylene chloride. The PMEC in the organic solvent can undergo a solvent exchange from the extracting organic solvent to methyl t-butyl ether (MTBE) and reacted with phosphoric acid to form the phosphate salt.

In some specific embodiments, piperazine is suspended in 4.0 volumes (V) of water at 20±5° C. Methyl chloroformate (1 equiv.) is added over ≥1 hour keeping the batch temperature ≤20° C. The reaction is agitated at 20±5° C. for ≥1 hour. One or more methylene chloride extractions are performed, with the methylene chloride layer being discarded each time. The aqueous layer is treated with a 10 M NaOH aqueous solution (0.8 equiv.) to adjust the pH to between 9.5 and 10.3. NaCl (1.47 equiv.) is added to the aqueous layer and methylene chloride washes (2×4V) are performed. The methylene chloride layers are combined and distilled to 2.5

V. Methyl butyl ether (MTBE) (8 V or 4.5 V) is added and the solution is concentrated to 2.5 V. MTBE (3.5 or 4.5 V) is added and concentrated to 2.5 V. MTBE (3.5 V) is added again and the mixture is polish filtered. The filtered solution is warmed to 45±5° C. (e.g., 40 to 50° C.) and a solution of 85% phosphoric acid (0.5 equiv.) in MTBE (1.5 V or 3.5 V) is added over ≥3 hours while maintaining a batch temperature of 45±5° C. (e.g., 40 to 50° C.). The suspension is cooled to 20±5° C. over 2 hours and agitated for 1 hour at 20±5° C. The suspension is filtered, and the resultant cake washed with MTBE (2 V) and dried (e.g., using nitrogen and vacuum for ≥24 h). Yield of PMEC phosphate hydrate is 48.5%, with 100% LC area %, 64.6 wt % assay, 4.2 wt % water content by Karl Fischer titration, 0.44 wt % residual MTBE, and 0.2% area % residual piperazine by GC.

Procedure for manufacture of PIPN from FNT: FNT can be brominated to form FNB, which can in turn be reacted with PMEC phosphate hydrate to form PIPN (see, e.g., top of Scheme 2). FNT can be brominated to form FNB via reaction with NBS and benzoyl chloride in acetic acid at a temperature of 70-95° C. FNB can be optionally extracted with toluene and/or washed with an aqueous basic solution to remove impurities. Alternatively, FNT can be brominated to form FNB via reaction with sodium bromate and sodium bisulfite in isopropyl acetate and water. FNB formed by reaction with sodium bromate and sodium bisulfite can optionally be washed with an aqueous solution of sodium thiosulfate and/or an aqueous solution of sodium chloride to remove impurities. FNB, regardless of how it is formed from FNT, can optionally be treated with diethylphosphite and a trialkylamine (e.g., triethylamine or diisopropylethylamine) at a temperature of 30 to 65° C. to reduce the undesired di-brominated impurity. FNB, regardless of how it is formed from FNT, can be admixed with a trialkylamine base (e.g., triethylamine or diisopropylethylamine) and PMEC phosphate hydrate to form PIPN. PIPN can be further converted to the hydrochloride salt form via admixing with hydrochloric acid, and can be further isolated.

In some specific embodiments, 2-fluoro-3-nitrotoluene (3.0 kg, 1 equiv) is charged to a reactor followed by benzoyl peroxide (0.03 equiv), and N-bromosuccinimide (0.56 equiv). Acetic acid (3 V) is charged to the reactor and the batch is heated to 83° C. After 1.5 h a slurry of NBS (0.56 equiv) in acetic acid (1 V) is charged to the reactor. After an additional 1.5 h a second slurry of NBS (0.56 equiv) in acetic acid (1 V) is charged to the reactor. After an additional 5 h a solution of $H_3PO_3$ (0.1 equiv) in acetic acid (0.1 V) is charged to the reactor and the batch is agitated for 30 minutes then cooled to 20° C. Water (5.5 V) and toluene (8 V) are charged to the reactor and the batch is agitated vigorously for 30 minutes. Agitation is then stopped and layers are allowed to separate. The lower aqueous layer is discarded. A solution of NaOH (1.7 equiv) in water (7 V) is charged to the reactor while maintaining a batch temperature below 30° C. The batch is agitated vigorously for 30 minutes. Agitation is stopped and layers are allowed to separate. The batch is filtered into a clean reactor and the layers are allowed to separate. The lower aqueous layer is discarded. N,N-diisopropylethylamine (0.53 equiv) is charged to the reactor followed by methanol (0.23 V) and the batch is heated to 40° C. A solution of diethylphosphite (0.46 equiv) in methanol (0.23 V) is charged to the reactor and the batch is agitated for 3 h. The batch is cooled to 20° C. To a solution of 1 equiv. 2-fluoro-3-nitrophenylmethylbromide in toluene (9V), prepared by radical bromination of 2-fluoro-3-nitrotoluene is added 2.3 equiv. diisopropylethylamine at 20° C. To the stirring solution is added a solution of 1.05 equiv. PMEC phosphate hydrate in methanol (2.6V) dropwise. After stirring for ≥3 hours water (5V) is added and the layers are separated. The organic phase is washed twice with saturated aqueous $NH_4Cl$ (5V) then once with saturated aqueous $NaHCO_3$ (5V). After polish filtration the toluene layer is diluted with isopropanol (9.7V) and water (0.5V). The solution is warmed to 55° C. and concentrated HCl (0.15V) added over 30 minutes. The solution is seeded with PIPN-HCl (3 mol %) and held at 55° C. for 15 minutes. Additional concentrated HCl (0.62V) is added over the course of 4 hours. The solution is held at 55° C. for 15 minutes and cooled to 20° C. in ≥1 hour. The solution is stirred for 30 minutes and filtered. The crystals are washed twice with IPA (5.6V). The cake is dried under vacuum and nitrogen to afford PIPN-HCl (82% yield, 98.6 wt %, 99.6 LCAP).

In other specific embodiments, 2-fluoro-3-nitrotoluene (3.0 kg, 1 equiv) is charged to a reactor followed by benzoyl peroxide (0.03 equiv) and N-bromosuccinimide (NBS, 0.1 equiv). Acetic acid (2 V) is charged to the reactor and the mixture is heated to 83° C. The reaction mixture is agitated for 1.5 h and a slurry of NBS (0.4 equiv) in acetic acid (0.9 V) is added. The reaction mixture is agitated for 1.5 h and a second slurry of NBS (0.4 equiv) in acetic acid (0.9 V) is added. The reaction mixture is agitated for 1.5 h and a second slurry of NBS (0.8 equiv) in acetic acid (1.6 V) is added. Acetic acid (1.0 equiv) is added and the reaction mixture is agitated for 1.5 h and a solution of phosphorus acid ($H_3PO_3$, 0.1 equiv) in acetic acid (0.1 V) is charged to the reactor. The mixture is agitated for 60 minutes and cooled to 20° C. Water (5.5 V) and toluene (8 V) are added to the vessel and the biphasic mixture is agitated vigorously for 30 minutes. Agitation is stopped and layers are allowed to separate. The aqueous layer is discarded. A solution of sodium hydroxide (1.7 equiv) in water (7 V) is charged while maintaining the temperature below 30° C. The biphasic mixture is agitated vigorously for 30 minutes. Agitation is stopped and layers are allowed to separate. The biphasic mixture is filtered and the layers are allowed to separate. The aqueous layer is discarded. The reaction mixture is transferred to a separate clean vessel, the original vessel is rinsed with toluene (1.2 V), and the rinse volume is added to the reaction mixture. N,N-diisopropylethylamine (0.53 equiv) and methanol (0.23 V) are charged to the organic layer and the mixture is heated to 40° C. A solution of diethylphosphite (0.46 equiv) in methanol (0.23 V) is charged and the reaction mixture is agitated for 3 h. The mixture is cooled to 20° C. To the solution of FNB in toluene, prepared by radical bromination of 2-fluoro-3-nitrotoluene (FNT), is added diisopropylethylamine (2.3 equiv.) and toluene (1 V). The FNB solution is added to a solution of methanol (1.8 V) and PMEC phosphate hydrate (1.05 equiv). The original vessel which contained the FNB solution is rinsed with methanol (0.8 V), and the rinse volume is added to the reaction mixture. The reaction mixture is agitated for 4 hours at 25°

C. and water (5 V) is added while maintaining batch temperature below 30° C. The biphasic mixture is agitated for 30 minutes and the layers are separated. The organic phase is washed twice with 3 M aqueous ammonium chloride (5 V), and once with 1 M aqueous sodium bicarbonate (5 V). The reaction mixture is transferred to a separate clean vessel, the original vessel is rinsed with toluene (1 V), and the rinse volume is added to the reaction mixture. After polish filtration, isopropanol (9.7 V) and water (0.6 V) are added to the organic solution. The solution is warmed to 55° C. and aqueous 32 wt % hydrochloric acid (0.25 equiv) is added over 30 minutes. The solution is agitated at 55° C. for APYR Manufacture: 5-Amino-2-methylpyridine (APYR) is commercially available as a raw material, however it contains various amounts of hydrochloride salt (3-5 wt %) and is provided as a dark-brown or black material. In addition, it can contain multiple potentially genotoxic impurities, as depicted in Scheme 5. Consequently, in order to use APYR as a commercial API starting material having high and consistent purity, a purification protocol for APYR or a synthetic process to prepare APYR is desired.

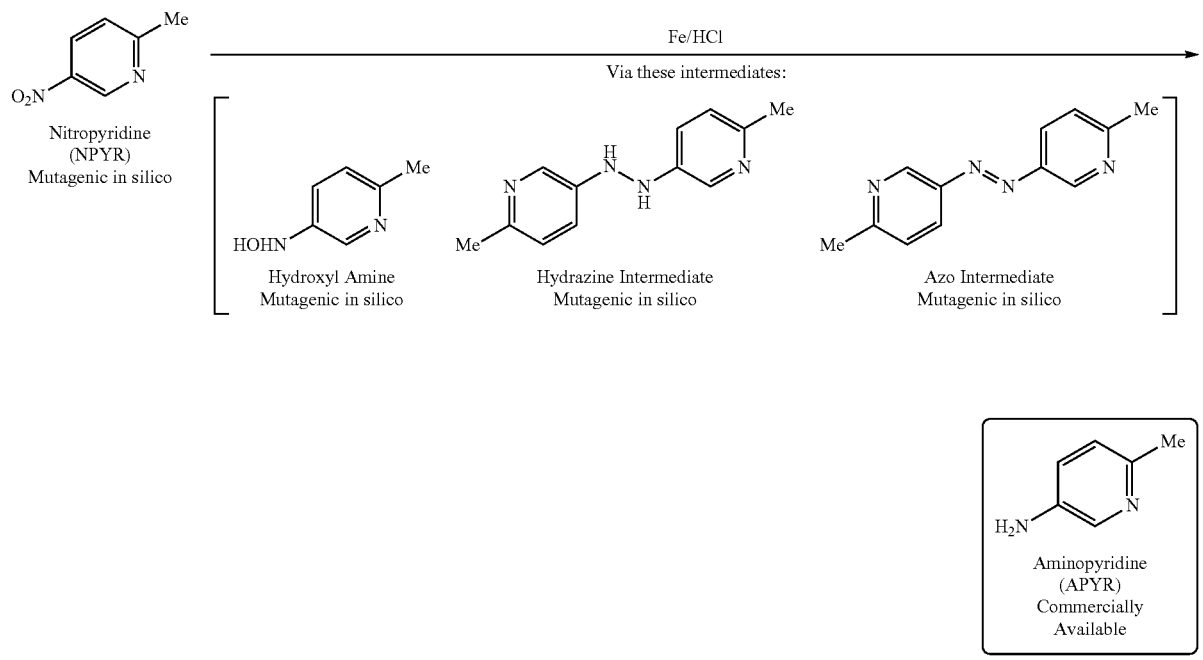

Scheme 5

15 minutes and seeded with a slurry of PIPN (hydrochloride salt, 0.045 equiv.) in isopropanol (0.2 V). The suspension is agitated at 55° C. for 30 minutes. Additional aqueous 32 wt % hydrochloric acid (1.0 equiv) is added over 4 hours. The suspension is agitated at 55° C. for 30 minutes and cooled to 20° C. in 2 hour. The suspension is agitated for 30 minutes and filtered. The product cake is washed twice with isopropanol (5.6 V). The product cake is dried on filter/drier to afford PIPN in 82% yield with 98.6 wt % assay and 99.6 LC area %.

In some specific embodiments, 2-Fluoro-3-NitroToluene (5.1 grams) is dissolved in isopropyl acetate (30 mL) and a solution of sodium bromate (14.9 grams) in water (50 mL) is added. The mixture is cooled to 10° C. A solution of sodium bisulfite (10.3 g) in water (100 mL) is added over 20 minutes. The resulting mixture is heated to 80° C. for 3 h. The reaction vessel has access to visible light. The contents are cooled to 20° C. and the phases separated. The organic phase is sequentially washed with 10% aqueous sodium thiosulfate and saturated aqueous sodium chloride. 1-(Bromomethyl)-2-fluoro-3-nitrobenzene (FNB) is obtained in 74% assay yield with 11% assay yield of the dibromide product.

Provided is a method of purifying APYR via washing an isopropyl acetate solution of APYR having up to 10 wt % of the corresponding hydrochloride salt with aqueous sodium hydroxide and then admixing the organic phase with charcoal. APYR can be crystallized from isopropyl acetate and heptane, optionally after azeotropic drying of the organic phase and polish filtration. The process to purify APYR is illustrated in Scheme 6. The purification of APYR involves the conversion of APYR hydrochloride salt to APYR freebase and concurrent removal of inorganic material using a basic aqueous sodium hydroxide wash of an isopropyl acetate solution of APYR. Following a charcoal treatment (e.g., mixing with charcoal and filtering of the suspension or recirculation of an isopropyl acetate solution through charcoal capsules), the solution comprising APYR is dried azeotropically and polish filtered. The clear isopropyl acetate solution is concentrated, and APYR is crystallized by addition of heptane. APYR is isolated in >99 LC area % and >99 wt % assay.

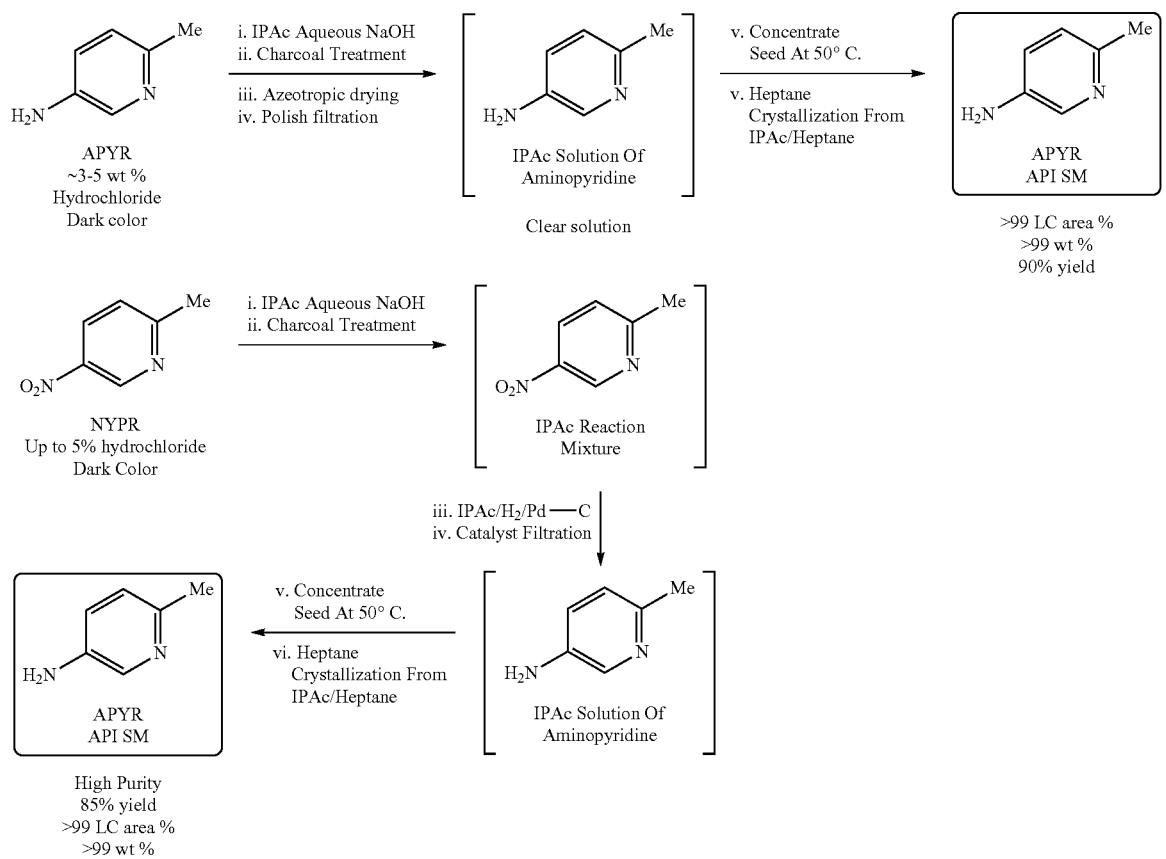

Scheme 6

In some specific embodiments, a solution of crude 5-Amino-2-methylpyridine (APYR) in isopropyl acetate (IPAc) (15 volumes) is washed with a 1N aqueous NaOH solution (1.0 volume) and circulated through charcoal capsules until the color-of-solution (COS) in process control is met (COS≤20). The solution is is azeotropically dried by concentration to approximately 6 volumes and isopropyl acetate (8 volumes) is added. The mixture is polish filtered into a separate vessel. The original vessel is rinsed with isopropyl acetate (1.0 volume), and the rinse volume is added to the reaction mixture. The solution is concentrated, e.g., by distillation under reduced pressure and the product is crystallized from isopropyl acetate and heptane (1:4, 10 vol). In some cases, the solution is concentrated to 3 volumes at 60° C. and seeded with purified APYR (1 mol %). The suspension is agitated for 30 minutes, cooled to 20° C. over 3 hours, and agitated for 1 hour. Heptane (8 volumes) is added over the course of 3 hours to complete the crystallization of material. The suspension is agitated for 1 hour, filtered, and the product cake is washed using heptane (2×3 volumes). Purified APYR is isolated by filtration, dried, and obtained in 90% yield with ≥99 LC area %.

APYR from NPYR: In some cases, APYR is synthesized from NPYR, as outlined in Scheme 6. NPYR is hydrogenated in the presence of a palladium catalyst to form crude APYR which can be crystallized from isopropyl acetate and heptane. The hydrogenation of NPYR to generate crude APYR is carried out after a basic aqueous wash and a charcoal treatment. Charcoal treatment comprises admixing with charcoal and filtering the suspension or recirculating an isopropyl acetate solution through charcoal capsules. The APYR solution is dried azeotropically and polish filtered. APYR is crystallized from isopropyl acetate and heptane. In some cases, the NPYR is purified before hydrogenation by washing with isopropyl acetate and aqueous sodium hydroxide and performing a charcoal treatment (admixing with charcoal then filtering off the charcoal).

In some specific embodiments, an isopropyl acetate (15 V) solution of 2-Methyl-5-nitropyridine (NPYR) is washed with a 1N aqueous NaOH solution (2 V) and water (2 V). The solution is optionally circulated through charcoal capsules until the color-of-solution (COS) in-process control is met (COS≤20). NPYR is hydrogenated with 4.5 bars hydrogen, e.g., at 70 psi/50-60° C. (e.g., 55° C.) in the presence of 5% Pd/C (on activated carbon sold by BASF Escat™ 1421, 1.5 wt % loading) for about 1 hour. The reaction mixture is filtered and azeotropically dried by concentration to about 7 V, addition of 8 V of isopropyl acetate, and polish filtration. The solution is concentrated to 3 V under reduced pressure at 60° C. The product is crystallized from isopropyl acetate and heptane (1:4) optionally by seeding with pure APYR (1 mol %) and/or optionally by cooling to 20° C. The product is optionally filtered and washed using heptane (2×3 V). APYR is isolated in 75% yield with ≥99 LC area %.

PCAR Manufacture: In the previously disclosed process for preparing omecamtiv mecarbil dihydrochloride hydrate, N-methylpyrrolidinone (NMP) is used as co-solvent in the preparation of PCAR. However, NMP is difficult to remove from the product cake as washing with 30 volumes of acetonitrile is necessary to reduce its level in the cake below 5000 ppm. Additionally, NMP is a potentially hazardous solvent that has been placed on REACH protocol lists regulated by the European Union, adopted to improve the protection of human health and the environment from the risks that can be posed by chemicals. It has been found that by using purified APYR prepared as described above, levels of APYR hydrochloride in isolated crystallized PCAR could easily be maintained below 1 LC area % without the use of NMP (see Scheme 7). This was not the case with un-purified APYR as 1 to 2 LC area % of APYR hydrochloride was found in isolated PCAR prepared without NMP from this starting material and constitutes a surprising finding.

Thus, provided herein is a method of preparing PCAR via admixing APYR and phenyl chloroformate in acetonitrile and in the absence of NMP. The reaction can occur at 15 to 30° C. for 1 to 15 hours. The method can use APYR that has been purified as noted above—e.g., to remove the APYR hydrochloride salt and dark color. APYR can be prepared from NPYR as described above. PCAR can be formed as its hydrochloride salt. The PCAR can be crystallized, e.g., as the hydrochloride salt.

In some specific embodiments, a solution of 5-Amino-2-methylpyridine (APYR) in ACN (15 volumes) is reacted with phenyl chloroformate (1.05 equiv.) for 3 hours at 20±5° C. while the product crystallizes from reaction mixture. The product slurry is filtered and the cake dried on filter/drier. PCAR is isolated in 97% yield, HPLC purity≥99%, APYR 0.3% and R-urea 0.25%. In some cases, to purified APYR is added acetonitrile (14 volumes) and the mixture is agitated for 30 minutes. The mixture is polished filtered into a separate vessel. The original vessel is rinsed with acetonitrile (1.0 volume), and the rinse volume is added to the reaction mixture. Phenylchloroformate (1.05 equiv.) is added over 5 hours at 20° C. in the presence of PCAR seeds (0.01 equiv). The mixture is agitated for an additional 2 hours. The product is isolated by filtration and the cake is washed with acetonitrile (2×2 volumes). The cake is dried on filter/drier. PCAR is isolated in 97% yield with ≥99 LC area % PCAR and 0.3 LC area % of residual APYR.

Scheme 7

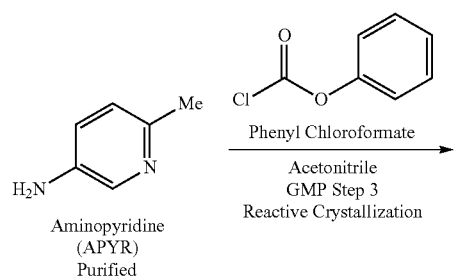

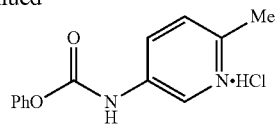

Phenyl Carbamate·HCl
(PCAR)
Crystalline GMP
Intermediate
95% Yield

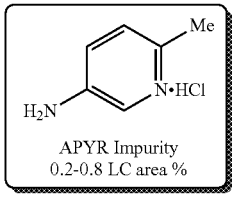

APYR Impurity
0.2-0.8 LC area %

PIPA Manufacture: The solvent used during the hydrogenation of PIPN to afford PIPA in the prior process to prepare omecamtiv mecarbil dihydrochloride hydrate was isopropyl acetate. The hydrogenation reaction proceeded well in this solvent, however an evaporative crystallization (distillation of solvent during the crystallization of the product) was necessary due to the high solubility of PIPA in mixtures of isopropyl acetate:heptane in ratios above 5:95. The high levels of isopropyl acetate used needed to be reduced by distillation after seeding of the product solution, thus leading to product fouling and lack of process robustness. For the process disclosed herein, isopropyl acetate has been replaced with toluene, eliminating all the problems stated above considering that the toluene:heptane ratio to be achieved immediately prior to filtration is 30:70, which eliminates an evaporative crystallization. In addition, ethanol is used as a co-solvent during the hydrogenation reaction in order to increase solubility of PIPA and ensure miscibility of the by-product in water. Finally, an aqueous sodium bicarbonate was replaced with an aqueous sodium hydroxide to operate the freebasing of PIPN for the commercial process in order to limit aqueous wash solution volumes and eliminate off-gassing. The process to prepare PIPA from PIPN as disclosed herein is presented in Scheme 8.

Scheme 8

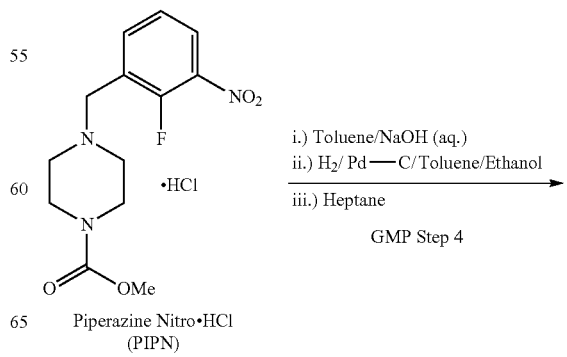

Piperazine Nitro·HCl
(PIPN)

i.) Toluene/NaOH (aq.)
ii.) H₂/Pd—C/Toluene/Ethanol
iii.) Heptane

GMP Step 4

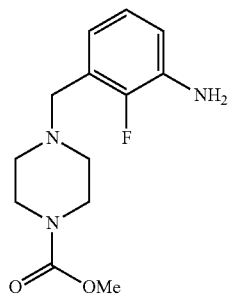

Piperazine Analine
(PIPA)
Crystalline GMP
Intermediate
90% Yield

Thus, provided herein is a method of synthesizing PIPA comprising admixing PIPN (which can comprise PIPN hydrochloride salt), an aqueous solution of an inorganic base, and toluene to form a PIPN freebase solution. The inorganic base can be sodium bicarbonate or sodium hydroxide, for example. In some embodiments, the inorganic base comprises sodium hydroxide. The PIPN freebase solution is then hydrogenated in the presence of a palladium catalyst in toluene and an alcohol solvent to form crude PIPA. The alcohol solvent can comprise ethanol or isopropanol. PIPA is then crystallized from a heptane and toluene solvent mixture.

In some specific embodiments, to a mixture of 1 equiv. PIPN-HCl and toluene (4V) is added 1 M aq. NaOH (3.3V) at 20° C. Stirring is continued for 1 hour before the phases are separated. The organic layer is washed twice with a mixture of water (2.4V) and saturated brine (0.6V), then the organic layer is distilled to 3.8V. The solution is filtered, the reactor rinsed with toluene (1V) and the rinse solution filtered before the organic layers are combined. To the toluene layer is added Pd/C (0.7 wt %) and the heterogeneous mixture is charged into a hydrogenation vessel. Ethanol (1V) is added to the mixture. Hydrogenation is performed at 20° C. under 60 psig of hydrogen. After the reaction is complete, the mixture is filtered and rinsed with toluene (1V). The mixture is distilled to 2.4V, seeded with 1 mol % PIPA in heptane (0.1V) at 35° C. and then cooled to 20° C. The addition of heptane (5.6V) is completed in 3 hours. The mixture is filtered and dried under vacuum and nitrogen to afford PIPA (90% yield, ≥97.0 wt %, ≥98.0 LCAP).

In some other specific embodiments, 1 N aqueous sodium hydroxide (3.3 volumes) is added to 1 equiv. of PIPN (hydrochloride salt) suspended in toluene (4 volumes). The biphasic mixture is agitated at 20° C. for 1 hour and the phases are allowed to separate. The organic layer is washed twice with a 0.9 M aqueous sodium chloride solution (3 volumes). The reaction mixture is azeotropically dried by concentration to approximately 3.8 volumes and polish filtered. The transfer line is rinsed with toluene (1 volume) and the rinse solution is combined with the PIPN solution. Ethanol (1 volume) is added to the PIPN solution and hydrogenation of the starting material is carried out in the presence of 5% Pd/C (on activated carbon sold by BASF as Escat 1421, 0.7 wt % catalyst loading) using a pressure of 4 bars of hydrogen at 15° C. Upon reaction completion, the mixture is filtered. The hydrogenation autoclave and filtered catalyst are rinsed with toluene (1V) and the rinse solution is combined with the reaction mixture. The solution is concentrated to 2.4 volumes and seeded with 1 mol % PIPA in heptane (0.1 volume) at 38° C. The mixture is agitated for 30 minutes at 38° C., cooled to 20° C. over the course of 2 hours, and agitated at that temperature for 30 minutes. Heptane is added (5.6 volumes) over the course of 3 hours and the mixture is agitated for 30 minutes. The mixture is filtered and dried on filter/drier. The cake is washed once with heptane:toluene (7:3, 2 total volumes) and once with heptane (2 volumes). PIPA is isolated in 88% yield with ≥98.0 wt % assay and ≥98.0 LC area %.

Preparation of omecamtiv mecarbil dihydrochloride hydrate: The prior process to prepare omecamtiv mecarbil dihydrochloride hydrate involved a telescoped procedure by which the omecamtiv mecarbil is prepared as a solution in THF, and the solvent is subsequently exchanged for isopropanol. However, considering that the solubility of omecamtiv mecarbil in isopropanol at 20° C. is about 10 mg/mL and the total volume of isopropanol at the end of the solvent exchange, 95% of the material is out of solution at the end of the solvent exchange, leading to the formation of a slurry that is difficult or impossible to stir. Distillation can no longer be performed once this slurry is formed due to poor mass transfer, leaving behind THF levels in the slurry that are above the in-process control (IPC) specification, e.g., greater than or equal to 1 GC area %. In practice, this leads to delays in the manufacturing due to necessary recharging of isopropanol until the mixture can be stirred, followed by additional distillation and analysis of residual THF. In addition, the ratio of isopropanol and water has to be verified using an in-process control considering the variable amounts of isopropanol at the end of the distillation and the influence of the solvent ratio (isopropanol/water) on the mother liquor losses upon filtration.

Considering the challenges presented by the telescoped process previously reported, an isolation of omecamtiv mecarbil freebase has been developed as disclosed herein (see Scheme 9). After formation of omecamtiv mecarbil in acetonitrile and THF, water is added and omecamtiv mecarbil freebase is isolated, e.g., via crystallization. The crystal agglomerates undergo rapid filtration and drying. Omecamtiv mecarbil freebase is then dissolved in isopropanol and water in the presence of hydrochloric acid to prepare omecamtiv mecarbil dihydrochloride hydrate. Using this modified procedure, the challenging solvent exchange is avoided and measurement of the ratio of isopropanol and water is unnecessary since known quantities of both solvents are added to crystalline omecamtiv mecarbil freebase at the beginning of the salt formation step.

Scheme 9

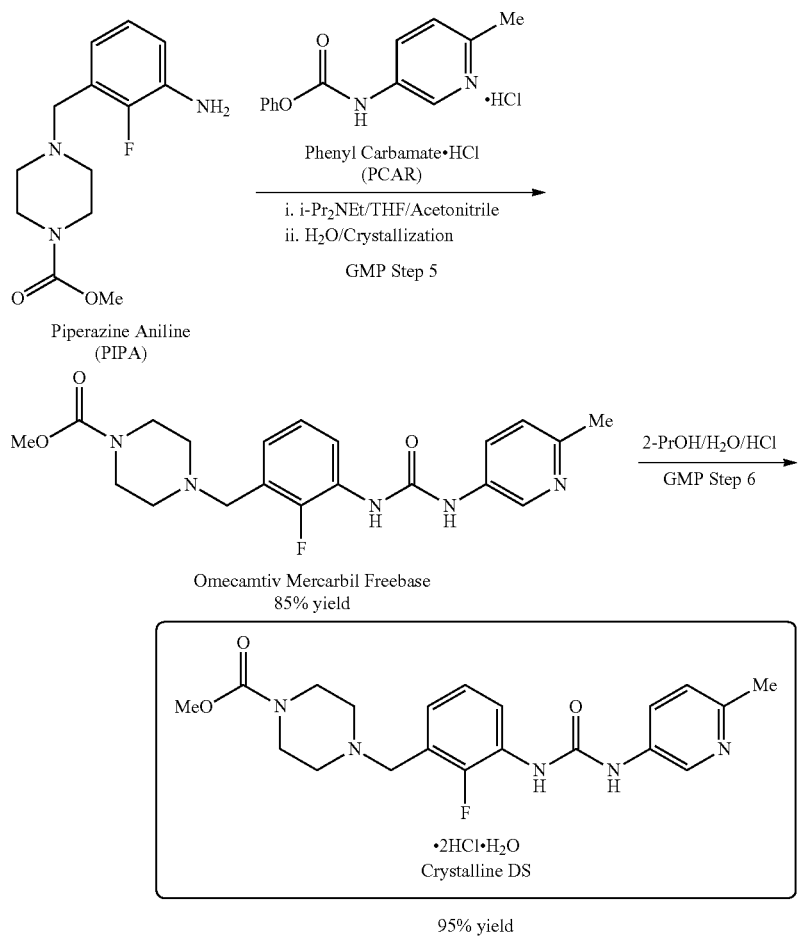

Thus, provided herein is a method of preparing omecamtiv mecarbil dihydrochloride hydrate via admixing PIPA, PCAR, and a trialkylamine (e.g., triethylamine or diisopropylethylamine) in acetonitrile and THF to form omecamtiv mecarbil. The omecamtiv mecarbil is isolated as the free base and then admixed with 2 to 3 molar equivalents of hydrochloric acid in isopropanol and water to form omecamtiv mecarbil dihydrochloride hydrate, which can optionally be crystallized from isopropanol and water. Isolation of the omecamtiv mecarbil free base can be performed via crystallization by addition of water and filtration. PIPA and PCAR can be prepared as disclosed above.

In some embodiments, PIPA (2.1 kg, 1 equiv) is charged to a reactor, followed by PCAR (1.1 equiv), then THF (2.5 V), and finally acetonitrile (2.5 V). To the resulting slurry is added N,N-diisopropylethylamine (1.2 equiv) and the batch is heated to 55° C. for 16 h. Water (5 V) is then added over 15 minutes and omecamtiv mecarbil freebase seeds (0.05 equiv) are charged to the reactor. The batch is agitated for 15 minutes and water (10 V) is added over 3 h. The batch is cooled to 20° C. over 1 h and filtered. The cake is washed with 3:1 water:acetonitrile (3 V) and then acetonitrile (3×3 V). The cake is dried in a filter/drier. Omecamtiv mecarbil freebase is isolated as a solid in 80% yield, with 99.9 LC area %, and 99.3 wt % assay.

Omecamtiv mecarbil freebase (2.6 kg, 1 equiv) is charged to a reactor followed by 2-propanol (2.6 V) and water (1.53 V). The batch is then heated to 45° C. 6 M aqueous HCl (2.2 equiv) is added at a rate to keep batch temperature below 60° C. The batch is heated to 60° C. for 30 minutes and filtered into a clean reactor at 60° C. The original vessel is rinsed with an isopropanol:water mixture (1:1, 0.1 volume total) and the rinse volume is added to the reaction mixture. The solution is cooled to 45° C. and a slurry of omecamtiv mecarbil dihydrochloride hydrate seed (0.05 or 0.03 equiv) in isopropanol (0.14 or 0.1 V) is charged to the reactor. The suspension is agitated for 1 h. Isopropanol (3.68 V) is charged to the reactor over 2 h. The mixture is warmed to 55° C. over 1 h and held for 30 minutes at that temperature. The mixture is cooled to 45° C. over 1 h. The mixture is agitated for 2 h and then isopropanol (7.37 V) is added to the reactor over 3 h. The mixture is agitated for 1 h and then cooled to 20° C. over 2 h. The mixture is wet milled until d90 specifications are met (e.g., ≤110 μm) and the suspension is filtered. The wet cake is washed twice with isopropanol:water (95:5, 2V). The wet cake is dried under vacuum until isopropanol levels are below 1000 ppm. The cake is optionally re-hydrated if necessary using e.g., a stream of humidified nitrogen, until the water content of the solids are between 3.0 and 4.2 wt %. The material can be recrystallized if it doesn't meet specification. Omecamtiv mecarbil dihydrochloride hydrate is isolated as a solid in 91.3% yield, with 99.96 LC area %, and 100.1 wt % assay.

Omecamtiv Mecarbil Dihydrochloride Hydrate Preparation using Continuous Manufacturing: Provided herein is a method of preparing omecamtiv mecarbil dihydrochloride hydrate using a continuous manufacturing process. The general synthetic procedure is outlined in Scheme 10 below.

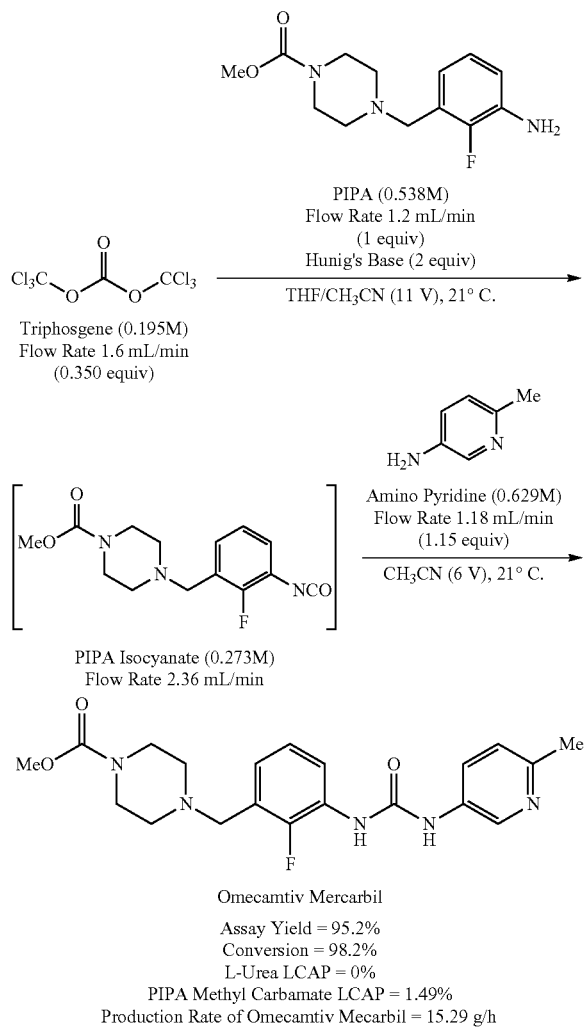

Thus, provided herein is a method for preparing omecamtiv mecarbil dihydrochloride hydrate comprising admixing PIPA, triphosgene, and a trialkylamine in acetonitrile and tetrahydrofuran to form a PIPA isocyanate; admixing PIPA isocyanate and APYR to form omecamtiv mecarbil free base; and admixing the omecamtiv mecarbil free base with 2 to 3 molar equivalents of hydrochloric acid in isopropanol and water to form omecamtiv mecarbil dihydrochloride hydrate. The reaction of PIPA, triphosgene and the trialkylamine (e.g., triethylamine or diisopropylethylamine) can be performed via continuous manufacturing using a micromixer and reaction loop. The reaction of PIPA isocyanate and APYR can be performed via continuous manufacturing using a Y-mixer and a reaction loop. PIPA and/or APYR can be prepared as described above.

In some embodiments, the continuous manufacture is performed as follows. To a 3-neck 1 L flask is added acetonitrile (471 mL) followed by PIPA (100.09 g, 374 mmol) and the mixture is stirred until solids dissolve. Diisopropylethylamine (135 ml, 770 mmol) is added and the mixture stirred until homogenous. To a separate 3-neck 1 L flask is added THF (620 mL) followed by triphosgene (39.3 g, 131 mmol) and the mixture is agitated until solids dissolve. To a separate 3-neck 1 L flask is added the acetonitrile (598 mL) followed by APYR (47.3 g, 431 mmol). The mixture is stirred until solids dissolve. The flasks are attached to the Asia syringe pumps. The flow of the PIPA/diisopropylethylamine solution is started at 1.2 mL/min (1.00 equiv PIPA) and the triphosgene solution flow started at 1.16 mL/min (1.05 equiv of phosgene). The process streams are mixed through a micromixer and then passed through a 3 mL reaction loop. Conversion of PIPA to the corresponding isocyanate is monitored by ReactIR. Steady state is reached almost instantly.

The APYR solution flow is started at 1.18 mL/min (1.15 equiv). The PIPA isocyanate and APYR streams are joined at a Y-mixer and passed through a 51 mL reaction loop equipment (e.g., a three loop system with a first loop having a volume of 10 mL, a second loop 25 mL, and a third loop 16 mL). The reaction stream is passed through the ReactIR flow cell to monitor reaction progress and collected in a vessel containing MeOH (100 mL). This set up is run continuously for 5.5 h to afford approximately 1.3 L of reaction product solution.

In some cases, the product solution is transferred to a 2 L reaction vessel and concentrated to a volume of approximately 350 mL. Isopropanol is added (300 mL) and the mixture is concentrated to a volume of 350 mL. The last operation is repeated three times.

After the final distillation, the vessel is backfilled with nitrogen and an additional 300 mL of isopropanol is added followed by 125 mL of water. The jacket temperature is set to 50° C. and 6 M HCl (82 mL) is slowly added. The jacket temperature is reduced to 45° C. and a 1:1 solution of isopropanol:water (50 mL) is added. The crystallization is seeded with an additional 5 g of omecamtiv mecarbil dihydrochloride hydrate suspended in 15 mL isopropanol, then held for 1 hour at 45° C. Isopropanol (227 mL) is added to the mixture and the temperature is raised to 55° C. for 1 hour. The jacket temperature is set to 45° C. and and the mixture stirred approximately 16 h. Isopropanol (670 mL) is added over 90 minutes. The jacket temperature is reduced to 20° C. and the mixture stirred for 2 hours. The slurry is filtered, and the cake is washed with 800 mL of 95:5 isopropanol:water. The cake is dried under vacuum. Omecamtiv mecarbil dihydrochloride hydrate is isolated in 93.5% yield (99.09 g) with 99.17 wt. % and 99.7% LCAP purity.

In some cases, to the reaction mixture are added isopropanol (315 mL) and water (125 mL). The mixture is heated to 50° C. and 6 M aqueous hydrochloric acid (82 mL) is added. The solution is cooled to 45° C. and a slurry of omecamtiv mecarbil dihydrochloride hydrate seed (5 g) in isopropanol:water mixture (1:1, 50 mL) is added. The suspension is agitated at 45° C. for 1 hour. Isopropanol (227 mL) is added and the mixture is warmed to 55° C. for 1 hour. The suspension is cooled to 45° C. and agitated for 16 hours. Isopropanol (670 mL) is added over 90 minutes. The mixture is cooled to 20° C. and agitated for 2 hours. The slurry is filtered and the cake washed with a solution of 95:5 isopropanol:water (800 mL). The cake is dried on the filter/drier. Omecamtiv mecarbil dihydrochloride hydrate is isolated in 93.5% yield (99.1 g) with 99.17 wt. % assay, and 99.7 LC area %.

A number of processes disclosed herein include steps noted as optional. In some cases, the optional step is not performed. In other cases, the optional step is performed.

What is claimed:

1. A process for synthesizing phenyl (6-methylpyridin-3-yl) carbamate

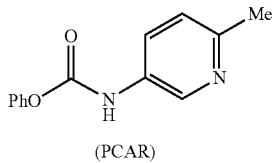 [SMILES: Cc1ccc(NC(=O)Oc2ccccc2)cn1]

(PCAR)

comprising admixing 5-amino-2-methylpyridine

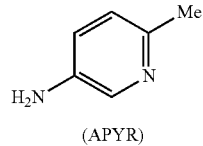

(APYR)

and phenyl chloroformate in acetonitrile to form PCAR, wherein the admixing is performed in the absence of N-methyl pyrrolidinone (NMP) and wherein purity of the APYR is ≥99 LC area %.

2. The process of claim 1, wherein the admixing is performed at a temperature of 15 to 30° C. for 1 to 15 hours.

3. The process of claim 1, wherein the PCAR is formed as a hydrochloride salt.

4. The process of claim 1, further comprising preparing APYR by a process comprising:
   (i) hydrogenating 2-methyl-5-nitropyridine

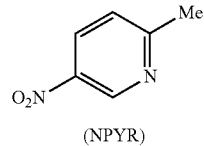

(NPYR)

in the presence of a palladium catalyst to form crude APYR; and
   (ii) crystallizing APYR from the crude APYR in isopropyl acetate and heptane.

5. The process of claim 4, further comprising, prior to step (i), washing NPYR in isopropyl acetate with aqueous sodium hydroxide, followed by admixing the washed NPYR in isopropyl acetate with charcoal.

6. The process of claim 1, further comprising, prior to admixing APYR and phenyl chloroformate, purifying APYR by a process comprising:
   (i) washing an isopropyl acetate solution of crude APYR, wherein the crude APYR comprises up to 10 wt % APYR hydrochloride, with aqueous sodium hydroxide, and admixing the washed APYR with charcoal to form an APYR solution after filtration; and
   (ii) crystallizing APYR from the APYR solution of step (i) from isopropyl acetate and heptane.

7. The process of claim 1, further comprising crystallizing PCAR.

* * * * *